United States Patent [19]
Gaullier et al.

[11] Patent Number: 5,393,895
[45] Date of Patent: Feb. 28, 1995

[54] PROCESS FOR OBTAINING 10-DEACETYLBACCATIN III

[75] Inventors: Jean-Claude Gaullier, Champs Sur Marne; Bernadette Mandard, Alfortville; Rodolphe Margraff, Viry Chatillon, all of France

[73] Assignee: Rhone-Poulenc Rorer, S.A., Antony Cedex, France

[21] Appl. No.: 10,083

[22] Filed: Jan. 27, 1993

[30] Foreign Application Priority Data

Oct. 5, 1992 [FR] France .................................. 92 11746

[51] Int. Cl.⁶ .......................................... C07D 305/14
[52] U.S. Cl. .................................................... 549/510
[58] Field of Search .......................... 568/705; 549/510

[56] References Cited

U.S. PATENT DOCUMENTS 4,814,470  3/1989  Colin et al. .......................... 514/449

*Primary Examiner*—Joseé G. Dees
*Assistant Examiner*—Joseph M. Conrad, III
*Attorney, Agent, or Firm*—Morgan & Finnegan

[57] ABSTRACT

This invention relates to a process for obtaining 10-deacetylbaccatin III from various parts of yew (Taxus sp.) by extraction and selective crystallization starting with a methanolic extract of the vegetable matter.

23 Claims, No Drawings

PROCESS FOR OBTAINING 10-DEACETYLBACCATIN III

FIELD OF THE INVENTION

The present invention to a process for selectively obtaining intermediates used for the preparation, by semisynthetic processes, of taxol, Taxotère or their analogues from various parts of plants containing these intermediates.

More particularly, the invention relates to the preparation of 10-deacetylbaccatin III from the bark, the trunk, the roots or the foliage of various species of yew.

BACKGROUND OF THE INVENTION

Taxol and Taxotère and their analogues of general formula:

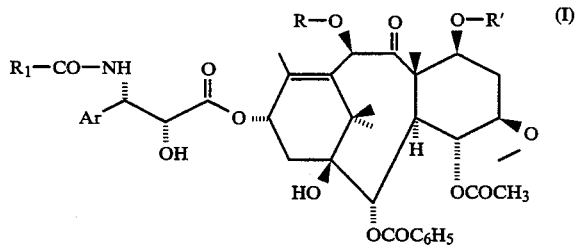

which exhibit remarkable anticancer and antileukaemia properties, constitute remarkable chemotherapeutic agents for the treatment of a certain number of cancers such as, for example, cancers of the breast, of the prostate, of the colon, of the stomach, of the kidney or of the testicles and more especially cancer of the ovary.

In particular, in the general formula (I), Ar may denote an optionally substituted phenyl radical, R may denote a hydrogen atom or an acetyl radical or an N-substituted carbamoyl radical, R' denotes a hydrogen atom or an N-substituted carbamoyl radical and $R_1$ may denote a phenyl radical or a radical $R_2$—O— in which $R_2$ denotes an alkyl, alkenyl, alkynyl, cycloalkyl, cycloalkenyl, bicycloalkyl, phenyl or heterocyclyl radical.

Taxol corresponds to the product of general formula (I) in which Ar and $R_1$ denote a phenyl radical and R denotes an acetyl radical and R' denotes a hydrogen atom, and Taxotère corresponds to the product of general formula (I) in which Ar denotes a phenyl radical, R and R' denote a hydrogen atom and $R_1$ denotes a t-butoxy radical.

Taxol, which exists in the natural state in various species of yew, in which it is present in small quantities, is difficult to isolate without effecting a complete destruction of the plant. For example, taxol can be isolated by the method of C. H. O. Huang et al., J. Natl. Prod., 49, 665 (1986), which consists in treating ground bark of *Taxus brevifolia* with methanol, concentrating the extract, extracting the concentrate with dichloromethane, reconcentrating, dispersing the residue in a hexane-acetone mixture (1—1 by volume), purifying the soluble part by chromatography on a Florisil column to obtain crude taxol, which is purified by successive recrystallizations from methanol-water and hexane-acetone mixtures and then by chromatography and further crystallization. The quantities of taxol which are thus extracted can represent from 0.005 to 0.017% of the part of the plant used.

Taxotère, which does not exist in the natural state, can be prepared by partial synthesis from 10-deacetylbaccatin III of formula:

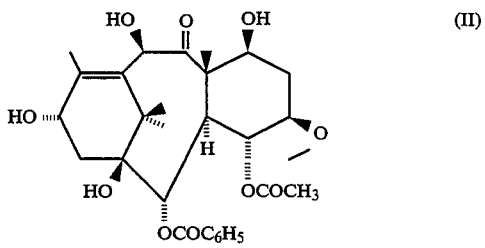

by processes which are described, for example, in U.S. Pat. Nos. 4,814,470 or 4,924,012 or in International Application PCT WO 92/09589.

Taxol can also be prepared by processes which involve the use of 10-deacetylbaccatin III either by going through the Taxotère intermediate under the conditions described in U.S. Pat. No. 4,857,653 or by esterification of baccatin III under the conditions described in European Patents EP 400,971 or EP 428,376 or by esterification of 10-deacetylbaccatin III and acetylation under the conditions described in U.S. Pat No. 4,924,011.

The different varieties of yew (*Taxus baccata, Taxus brevifolia, Taxus canadensis, Taxus cuspidata, Taxus floridana, Taxus media* and *Taxus wallichiana*) contain taxane derivatives, the main ones of which are essentially taxol and 10-deacetylbaccatin III, the other derivatives being more particularly cephalomannin, 10-deacetylcephalomannin or baccatin III, optionally bonded to sugars.

Whereas taxol is present mainly in the trunk and the bark, 10-deacetylbaccatin III is present essentially in the foliage. Furthermore, the content of 10-deacetylbaccatin III in the foliage is generally much higher than that of taxol, whether the latter be present in the bark, the trunk or in the foliage.

As a result, it is particularly important to be able to have access to 10-deacetylbaccatin III, which is essential for the preparation of much larger quantities of taxol than by direct extraction from yew, and for the preparation of Taxotère.

Extraction of 10-deacetylbaccatin III from yew foliage does not result in a total destruction of the plant, the foliage of which can be employed again after each growth cycle.

In general, the known methods for extracting taxane derivatives present in various parts of the yew (bark, trunk, roots, foliage, etc.) require the use of long and costly chromatographic techniques which do not permit a complete and quantitative separation of the taxane derivatives initially present in the plant.

According to the process described in U.S. Pat No.4,814,470, which employs wet grinding of the needles in ethanol, an extraction with an organic solvent such as methylene chloride and successive chromatographies, it is possible to isolate approximately 40 % of the 10-deacetylbaccatin III present in the foliage.

The various constituents derived from taxane which are present in the various parts of the yew can also be separated by methods employing reverse liquid phase chromatography, which are described in particular in international application PCT WO 92/07842. These processes consist essentially in treating the crude extracts of yew by reverse liquid phase chromatography on an adsorbent on which the taxane derivatives are immobilized, in eluting the taxane derivatives and in isolating them. According to this process it is possible to isolate approximately 25% of the 10-deacetylbaccatin III present in the foliage.

DESCRIPTION OF THE INVENTION

It has now been found, and this is what forms the subject of the present invention, that 10-deacetylbaccatin III can be extracted selectively from the various parts of yew, and more particularly the foliage, by a simple process which does not involve chromatographic techniques. For example, it is possible to extract approximately 75% of the 10-deacetylbaccatin III present in the foliage.

More particularly, the process according to the invention consists:

1) in treating the ground parts of yew (Taxus sp.) with an aliphatic alcohol so as to obtain an alcoholic extract containing 10-deacetylbaccatin III,
2) in diluting the alcoholic extract, optionally concentrated, with water,
3) in separating by filtration, sedimentation or centrifuging the insolubles present in the hydroalcoholic solution obtained,
4) in removing virtually all of the alcohol from the hydroalcoholic solution,
5) in extracting 10-deacetylbaccatin III from the aqueous phase thus obtained with a suitable organic solvent,
6) in removing the solvent from the organic extract thus obtained containing 10-deacetylbaccatin III,
7) in selectively crystallizing 10-deacetylbaccatin III from the residue thus obtained, in an organic solvent,
8) in isolating the purified 10-deacetylbaccatin III.

The process according to the invention can be applied to any appropriate part of yew, such as the bark, the trunk, the roots or the foliage. The yew employed for carrying out the process according to the invention preferably belongs to the *Taxus baccata, Taxus brevifolia, Taxus canadensis, Taxus cuspidata, Taxus floridana, Taxus media* or *Taxus wallichiana* variety. It is particularly advantageous to employ yew foliage (*Taxus baccata, Taxus brevifolia*) which is generally richer in 10-deacetylbaccatin III. For better application of the process it is preferable to employ the various parts of yew in a ground and optionally dried form. The fragments employed may vary from 0.5 to a few millimeters in size. For reasons of convenience it may be advantageous to employ fragments whose mean size is smaller than 1 mm. The ground and optionally dried parts of yew may be obtained by grinding and optionally drying operations which, optionally, precede or follow operations of freezing and thawing of the fresh parts of the plant or are interposed between the operations of freezing and thawing of the fresh parts of the plant.

The alcoholic extract is obtained by stirring a mixture, optionally heated, of the ground and optionally dried parts of yew with an alcohol which is generally chosen from methanol, ethanol, propanol, isopropanol and t-butanol. It is particularly advantageous to employ methanol.

The alcoholic extract containing 10-deacetylbaccatin III is diluted by adding water to give a hydroalcoholic solution.

To make use of the process it is advantageous to adopt special conditions of dilution and of alcohol content in the aqueous phase, so as to avoid the losses of 10-deacetylbaccatin III and to remove as large a quantity of insoluble products as possible. Under these conditions it may be necessary to concentrate the alcoholic extract containing 10-deacetylbaccatin III before dilution with water. More particularly, the dilution by the addition of water to the alcoholic extract optionally concentrated by distillation, preferably at reduced pressure, must be carried out in such a way that the ratio of the weight of the diluent mixture to the weight of the dry matter present in the alcoholic extract is between 4 and 8, the water-alcohol diluent mixture containing 10 to 30% by weight of alcohol.

The products which are insoluble in the hydroalcoholic solution thus obtained are removed by conventional techniques and preferably by filtration, by sedimentation or by centrifuging. When the removal is performed by filtration, it may be advantageous to operate in the presence of a filter medium such as infusorial earth (Celite) and of a flocculating agent.

The removal of the alcohol from the hydroalcoholic solution thus obtained is preferably performed by distillation, preferably at reduced pressure, optionally in the presence of an antifoaming agent, so as to avoid or to limit the thermal degradation of the constituents of the mixture.

In general, the 10-deacetylbaccatin III present in the aqueous solution thus obtained, in which the alcohol content is generally lower than 1%, is extracted, once or more times, with an organic solvent chosen from ethers such as methyl t-butyl ether, ethyl t-butyl ether, methyl n-butyl ether, methyl n-amyl ether, ethyl t-amyl ether, t-butyl isopropyl ether, ethyl isobutyl ether, t-butyl n-propyl ether or ethyl n-hexyl ether., and aliphatic esters such as ethyl acetate, propyl acetate, isopropyl acetate, n-butyl acetate, t-butyl acetate, methyl t-butylacetate, t-butyl propionate or t-amyl acetate. Methyl t-butyl ether, ethyl t-butyl ether, ethyl acetate and n-butyl acetate are of very particular interest. It is still more especially advantageous to employ ethyl acetate or n-butyl acetate.

The organic extracts are optionally washed with an aqueous solution of a weak base (for example aqueous sodium carbonate solution) and/or water. After drying, the organic solvent of the extract is removed by conventional methods and in particular by distillation, optionally at reduced pressure, to give a generally solid residue from which 10-deacetylbaccatin III is isolated.

The selective crystallization of 10-deacetylbaccatin III is performed from a solution of the residue obtained in an organic solvent or in a mixture of organic solvents. Solvents which permit the selective crystallization of 10-deacetylbaccatin III and which can be advantageously employed are nitriles such as acetonitrile or propionitrile, optionally mixed with an aliphatic alcohol such as methanol, ethanol, propanol, isopropanol or n-butanol or an aliphatic ester such as ethyl acetate, n-butyl acetate or t-butyl acetate or a ketone such as acetone, methyl ethyl ketone, methyl propyl ketone, methyl n-butyl ketone and methyl isobutyl ketone. It is particularly advantageous to perform the selective crystallization in acetonitrile, optionally in the presence of ethanol and/or acetone and/or ethyl acetate and/or n-butyl acetate.

The 10-deacetylbaccatin III which precipitates can be isolated by filtration, sedimentation or centrifuging.

The 10-deacetylbaccatin III obtained by the extraction process of the present invention can be employed for preparing taxol or Taxotère or their derivatives under the conditions described more particularly in patents EP 0,253,738, EP 0,253,739, EP 0,336,840, EP 0,336,841, WO 92/09589, EP 0,400,971 and EP 0,428,376.

EXAMPLES

The following examples illustrate the process according to the invention.

Example 1

200 liters of methanol, 1.4 kg of glass wool and 250 kg of ground yew leaves (*Taxus baccata*) whose mean particle size is close to 0.8 mm are placed in a percolator. 400 liters of pure methanol are added. The percolation is performed by feeding the percolator with fresh solvent via the top at a rate of 870 liters/hour and collecting the methanolic extract at the bottom of the percolator. The percolation last 5 hours at 20° C. The methanolic solution collected is evaporated at reduced pressure (70 –80 kPa) at 40° C in an evaporator to obtain a concentrate whose solids content is between 40 and 80% by weight.

A methanolic extract (prepared under the conditions described above) is employed, containing 353 g of dry extract, 420 g of methanol and 40 g of water, the quantity of 10-deacetylbaccatin III present being 1130 mg.

The methanolic extract is introduced into a 2-liter reactor, followed, with stirring, by 1590 $cm^3$ of water. The mixture is stirred for 1 hour and then 35 g of Celite are added successively with stirring for 1 hour and 25 $cm^3$ of "Zetag 87" flocculant. The final suspension obtained is filtered on a No. 4 glass sinter 130 mm in diameter. The insoluble products and the Celite are washed with 100 g of a water-methanol mixture (8–2 by weight).

The filtrate is placed in a 2-liter reactor and 2 $cm^3$ of Silicone 426R are added. The mixture is distilled at reduced pressure (7.3–11 kPa) at a temperature of between 35° and 42° C., the temperature of the outer bath being between 45° and 50° C. A distillate (909 g) and a concentrate (1432 g) containing 0.5% of methanol are obtained.

The concentrate is extracted once with 700 $cm^3$ of ethyl acetate then twice with 350-$cm^3$ portions of ethyl acetate. The combined organic phases are washed with 2 times 700 $cm^3$ of a 0.1M sodium carbonate solution, then once with 350 $cm^3$ of water. The pH is 8. The organic phase (1049 g) is concentrated to dryness at reduced pressure (1.33–21.3 kPa) at 40° C. 16.2 g of dry extract are thus obtained.

Example 2

Into a 500-$cm^3$ round bottom flask are introduced 45.5 g of dry extract containing 9.3% of 10-deacetylbaccatin III obtained under the conditions described in Example 1, and 18 $cm^3$ of ethyl acetate are then added. The homogeneous mixture is stirred and heated to 50° C. 136 $cm^3$ of acetonitrile are then added over 15 minutes at 50° C. The suspension is stirred for approximately 1 hour and is then cooled to a temperature close to 20° C. over approximately 3 hours. The precipitate is separated off by filtration on a No. 3 glass sinter (diameter: 35 mm) and is then washed with 20 $cm^3$ of acetonitrile and then with 2 times 20 $cm^3$ of diisopropyl ether. The product is dried at reduced pressure (1.33 kPa) at 40° C. for 20 hours. 5.2 g of a white product are thus obtained, containing 75.8% of 10-deacetylbaccatin III.

The crystallization yield is 93.6%.

Example 3

Into a 1-liter round bottom flask are introduced 275.2 g of an ethyl acetate solution of 39.6 g of dry matter containing 3.48 g of 10-deacetylbaccatin III. This solution is concentrated at reduced pressure (6.0 kPa). 164 g of ethyl acetate are collected. 36 $cm^3$ of ethanol are added to the concentrate and the mixture is cooled to 10° C. 60 $cm^3$ of acetonitrile are then slowly added (approximately ½ hour) with stirring (30 revolutions/minute). The suspension is stirred at 10° C. for 1 hour and 84 $cm^3$ of acetonitrile are then added rapidly. Stirring is continued at 10° C. for 15 hours. The precipitate is separated by filtration on a No. 3 glass sinter (diameter: 35 mm) and is then washed with 2 times 20 $cm^3$ of acetonitrile and then with 2 times 20 $cm^3$ of diisopropyl ether. The product is dried for 12 hours at reduced pressure (0.27 kPa) at 40° C. 2.85 g of a white crystalline powder containing 93.8% of 10-deacetylbaccatin III are thus obtained.

The crystallization mother liquors and the washings (247 g) are concentrated at reduced pressure (2.7 kPa) at 40° C. 36 g of dry material are thus obtained and are taken up with 18 $cm^3$ of ethanol. 72 $cm^3$ of acetonitrile are then added slowly. The mixture is stirred for 15 hours at a temperature close to 20° C. The precipitate is separated off by filtration and is washed with 2 times 5 $cm^3$ of acetonitrile and with 2 times 5 $cm^3$ of diisopropyl ether. After drying, 0.662 g of a fine powder containing 62.7% of 10-deacetylbaccatin III are obtained.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A process for obtaining 10-deacetylbaccatin III from various parts of yew (Taxus sp.), comprising:
   1) treating ground parts of yew with an aliphatic alcohol to obtain an alcoholic extract containing 10-deacetylbaccatin III,
   2) diluting the alcoholic extract with water to obtain an hydroalcoholic solution containing 10 to 30% by weight of alcohol and insolubles, wherein the ratio of the weight of the hydroalcoholic solution to the insolubles is between 4 and 8,
   3) separating off the insolubles present in the hydroalcoholic solution by filtration, sedimentation or centrifugation,
   4) removing virtually all of the alcohol from the hydroalcoholic solution to obtain an aqueous phase,
   5) extracting the 10-deacetylbaccatin III present in the aqueous phase with an organic solvent to obtain an organic extract,
   6) removing the organic solvent from the organic extract to obtain a residue,
   7) selectively crystallizing 10-deacetylbaccatin III from the residue, and purifying 10-deacetylbaccatin III.

2. A process according to claim 1, further comprising concentrating the alcoholic extract of step 1) prior to dilution with water.

3. A process according to claim 1, further comprising drying the ground parts of yew prior to treatment with aliphatic alcohol.

4. A process according to claim 1, wherein the alcoholic extract of step 1) is obtained by stirring the ground parts of yew in an aliphatic alcohol selected from the group consisting of methanol, ethanol, propanol, isopropanol, and t-butanol.

5. Process according to claim 1, wherein the aliphatic alcohol is methanol.

6. A process according to any one of claims 1, 2, or 3, wherein the ground or ground and dried parts of yew are obtained by grinding or grinding and drying operations which precede or follow the operations of freezing and thawing of the fresh parts of the plant or are interposed between operations of freezing and thawing of the fresh parts of the plant.

7. A process according to claim 1, wherein the alcoholic extract, is diluted with water so that the ratio of the weight of diluent mixture to the weight of dry matter present in the alcoholic extract is between 4 and 8 and the water-alcohol diluent mixture contains 10 to 30% of alcohol.

8. A process according to claim 7, further comprising concentrating the alcoholic extract prior to dilution with water.

9. Process according to claim 1 wherein the alcohol is removed from the hydroalcoholic solution by distillation.

10. A process according to claim 9, wherein the distillation is carried out at reduced pressure.

11. A process according to claim 1, wherein the organic solvent is selected from the group consisting of ethers and aliphatic esters.

12. A process according to claim 11, wherein the ethers are selected from the group consisting of methyl t-butyl ether, ethyl t-butyl ether, methyl n-butyl ether, methyl n-amyl ether, ethyl t-amyl ether, t-butyl isopropyl ether, ethyl isobutyl ether, t-butyl n-propyl ether, t-butyl isopropyl ether and ethyl n-hexyl ether.

13. A process according to claim 11, wherein the aliphatic esters are selected from the group consisting of ethyl acetate, propyl acetate, isopropyl acetate, n-butyl acetate, t-butyl acetate, methyl t-butylacetate, t-butyl propionate and t-amyl acetate.

14. A process according to claim 11, wherein the organic solvent is ethyl acetate or n-butyl acetate.

15. A process according to claim 1, wherein 10deacetylbaccatin III is selectively crystallized from an organic solvent selected from the group consisting of aliphatic nitriles, aliphatic nitriles mixed with an aliphatic alcohol, aliphatic nitriles mixed with an aliphatic ester, and aliphatic nitriles mixed with an aliphatic ketone.

16. A process according to claim 15, wherein the aliphatic nitriles are selected from the group consisting of acetonitrile and propionitrile.

17. A process according to claim 15, wherein the aliphatic alcohol is selected from the group consisting of methanol, ethanol, propanol, isopropanol, and n-butanol.

18. A process according to claim 15, Wherein the aliphatic ester is selected from the group consisting of ethyl acetate, isopropyl acetate, n-butyl acetate, and t-butyl acetate.

19. A process according to claim 15, wherein the ketone is selected from the group consisting of acetone, methyl ethyl ketone, methyl propyl ketone, methyl n-butyl ketone, and methyl isobutyl ketone.

20. A process according to claim 15, wherein the selective crystallization is performed in acetonitrile or acetonitrile combined with ethanol and/or ethyl or n-butyl acetate and/or acetone.

21. A process according to claim 1, wherein the purified 10-deacetylbaccatin III is isolated by filtration, sedimentation, or centrifugation.

22. A process according to claim 1, wherein the 10deacetylbaccatin III is extracted from yew foliage.

23. A process according to claim 22, wherein the yew belongs to the *Taxus baccata, Taxus brevifloria, Taxus canadensis, Taxus cuspidata, Taxus floridana, Taxus media,* or *Taxus wallichiana* variety.

* * * * *